(12) United States Patent
Cines et al.

(10) Patent No.: US 6,750,201 B1
(45) Date of Patent: Jun. 15, 2004

(54) COMPOSITIONS AND METHODS FOR PROMOTING INTERNALIZATION AND DEGRADATION OF UROKINASE-TYPE PLASMINOGEN ACTIVATOR

(75) Inventors: Douglas Cines, Wynnewood, PA (US); Abd Al-Roof Higazi, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/544,665

(22) Filed: Apr. 6, 2000

Related U.S. Application Data

(63) Continuation of application No. PCT/US98/21800, filed on Oct. 15, 1998.
(60) Provisional application No. 60/062,274, filed on Oct. 17, 1997.

(51) Int. Cl.[7] ............................. A61K 38/08; C07K 7/06
(52) U.S. Cl. ......................................... 514/17; 530/329
(58) Field of Search ............................... 514/17, 12, 13, 514/14, 15, 16; 530/329, 324, 325, 326, 327, 328

(56) References Cited

FOREIGN PATENT DOCUMENTS

| EP | 0 320 840 | | 6/1989 |
|---|---|---|---|
| WO | WO 91/05048 | * | 4/1991 |
| WO | WO 94/28145 | | 12/1994 |
| WO | WO 95/02413 | | 1/1995 |
| WO | WO 97/03704 | * | 2/1997 |

OTHER PUBLICATIONS

Ngo et al., 'Computational Complexity, Potein Sructure Prediction, and the Levinthal Paradox,' The Protein Folding Problem and Tertiary Structuer Prediction. Ed. K. Merz and L. Le Grand. BirkHauser, Boston MA. pp. 491–495. 1994.*
Rudinger, J. (1976). Peptide Hormones (ed. J.A. Parsons). University Park Press. Baltimore. pp 1–7, 1976.*
Anti–angiogenesis–Cutting off cancer's fuel line. Mayo–Clinic Available online, website: <www.slip.net/~mcdavis/database/angio153.htm>. Last Updated: May 12, 1998. Accessed on Apr. 1, 2002.*
Black, H. 'Angiogenesis–Promoting and Blocking–Comes into Focus' The Scientist, vol. 12, 9, p. 1–4, Apr. 27, 1998.*
Golden, Frederic, "Of Mice and Men: Don't Blame the Rodents" Time, pp. 40–46. May 1998.*
Gura, Trisha "Systems for Identifying New Drugs Are Often Faulty" Science, vol. 278, 1041–1042, Nov. 1997.*
Dermer, Gerald "Another Anniversary for the War on Cancer", Biotechnology, vol. 12, p. 320. Mar. 1994.*
Ngo, Marks and Karplus (1994) Computational Complexity, protein Structure Prediction, and the Levinthal Paradox, in The Protein Folding Problem and Tertiary Structure Prediction, Kenneth Merz, Jr. and Scott LeGrand, eds. pp. 1–80, 1994.*

* cited by examiner

Primary Examiner—Leon B. Lankford, Jr.
Assistant Examiner—Anish Gupta
(74) Attorney, Agent, or Firm—Morgan, Lewis & Bockius LLP

(57) ABSTRACT

The invention includes compositions and methods for promoting internalization and degradation of urokinase-type plasminogen activator.

5 Claims, 8 Drawing Sheets

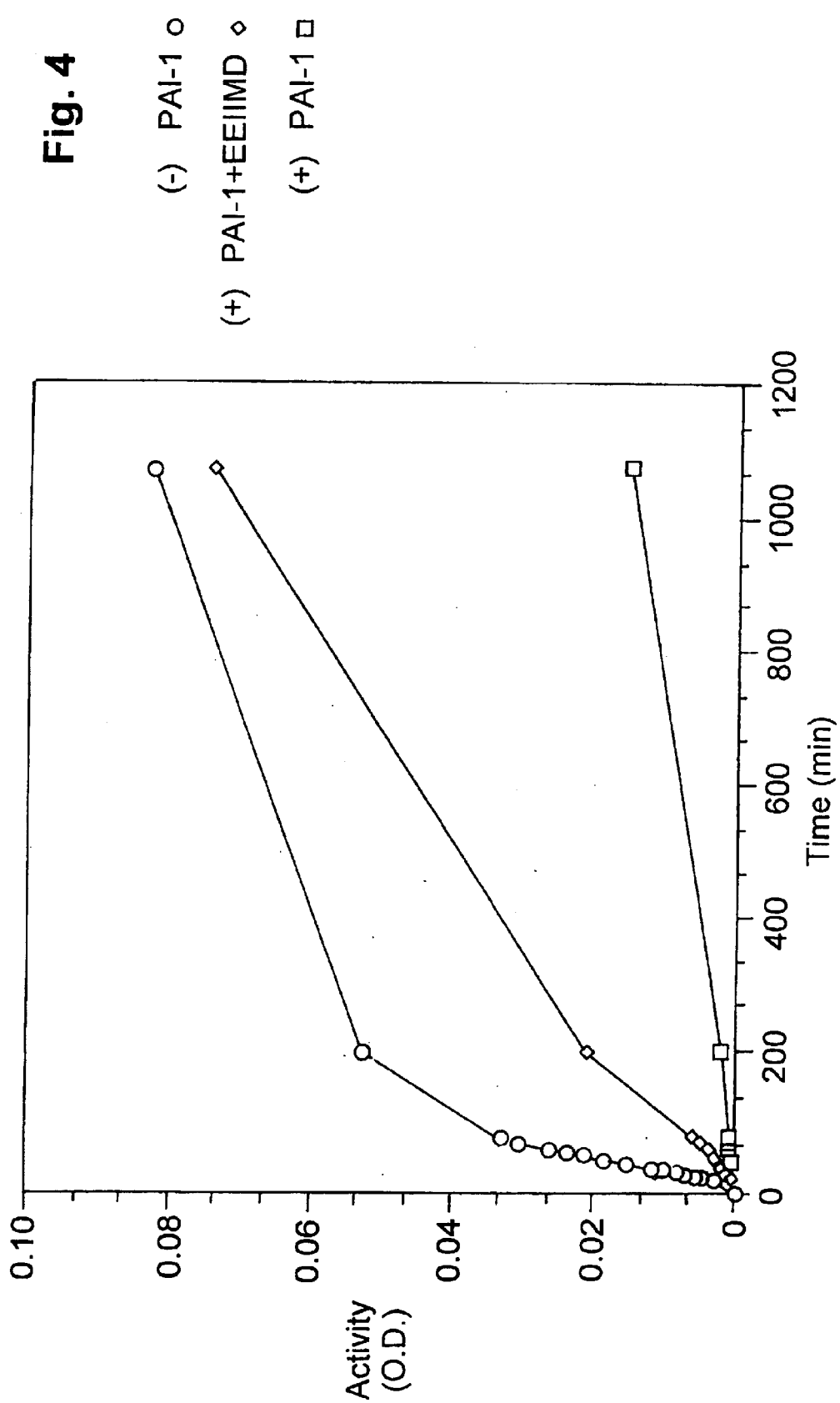

SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Residues
      179-184 of urokinase-type plasminogen activator

<400> SEQUENCE: 1

Arg His Arg Gly Gly Ser
 1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Residues
      346-356 of plasminogen activator inhibitor-1

<400> SEQUENCE: 2

Arg Met Ala Pro Glu Glu Ile Ile Met Asp Arg
 1               5                  10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Peptide for
      modulating binding of scuPA with LM-TK(-) cells

<400> SEQUENCE: 3

Glu Glu Ile Ile Met Asp
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Peptide for
      modulating binding of scuPA with LM-TK(-) cells

<400> SEQUENCE: 4

Arg Glu Ile Ile Met Asp
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Peptide for
      modulating binding of scuPA with LM-TK(-) cells

<400> SEQUENCE: 5

Glu Glu Ile Ile Met Arg
 1               5

COMPOSITIONS AND METHODS FOR PROMOTING INTERNALIZATION AND DEGRADATION OF UROKINASE-TYPE PLASMINOGEN ACTIVATOR

CROSS-REFERENCE TO RELATED APPLICATIONS

This application is a continuation of international patent application PCT/US98/21800, filed on Oct. 15, 1998.

This application is entitled to priority pursuant to 35 U.S.C. §119(e) to U.S. provisional patent application No. 60/062,274, which was filed on Oct. 17, 1997.

FIELD OF THE INVENTION

The field of the invention is regulation of cell adhesion and migration.

BACKGROUND OF THE INVENTION

Plasminogen activators convert the inactive zymogen plasminogen into the broad-spectrum proteolytic enzyme, plasmin (Higgins et al., 1990, Annu. Rev. Pharmacol. Toxicol. 30:91–121; Holden, 1990, Radiology 174:993–1001; Mayer, 1990, Clin. Biochem. 23:197–211). One type of plasminogen activator, designated urokinase-type plasminogen activator (uPA), is a component of the circulatory system and other fluid compartments of the mammalian body.

uPA is the principal cell-associated plasminogen activator and has been implicated in several biological processes including angiogenesis, organogenesis, ovulation, inflammation, cancer, tumor cell invasion and metastasis, atherosclerosis, and other biological and pathological processes characterized by cell migration through physiological barriers such as fibrin and basement membranes (Gyetko et al., 1994, J. Clin. Invest. 93:1380–1387; Gyetko et al., 1996, J. Clin. Invest. 97:1818–1826; Shapiro et al., 1997, Am. J. Pathol. 150:359–369; Dado et al., 1994, Fibrinolysis 8(Suppl. 1):189–203).

uPA is synthesized as a single chain zymogen, designated single chain uPA (scuPA), which exhibits little urokinase activity (Ellis et al., 1987, J. Biol. Chem. 262:14998–15003; Petersen et al., 1988, J. Biol. Chem. 263:11189–11195; Husain, 1991, Biochemistry 30:5707–5805; Colleen et al., 1986, J. Biol. Chem. 261:1259–1266). Activation of scuPA occurs by enzymatic cleavage of scuPA, yielding two-chain uPA (tcuPA). Physiological formation of tcuPA from scuPA is catalyzed primarily by plasmin (Robbins et al., 1967, J. Biol. Chem. 242:2333–2342). scuPA may also be activated by binding of scuPA to the cell-surface receptor, uPAR. In the case of scuPA binding to uPAR, scuPA remains a single chain molecule, but is active (Higazi et al., 1995, J. Biol. Chem. 270:17375–17380).

The activity of uPA is regulated, in part, by plasminogen activator inhibitor-1 (PAI-1), which is a member of the serine protease inhibitor (SERPIN) family of proteins (Kruithof, 1988, Enzyme 40:113–121; Potempa et al., 1994, J. Biol. Chem. 269:15957–15960; Lijnen et al., 1994, Eur. J. Biochem. 224:567–574). PAI-1 is thought to be the most relevant inhibitor of uPA activity in the fluid phase, due to its high second order rate constant of inhibition, $1.7 \times 10^{-8}$ $M^{-1}.s^{-1}$, which is higher than any other protease inhibitor (Hekman et al., 1988, Arch. Biochem. Biophys. 262:199–210).

A soluble recombinant form of uPAR, designated suPAR, is known and differs from uPAR by lacking the portion of uPAR that links the receptor to the cell surface. suPAR possesses the same properties as uPAR with respect to binding and activating scuPA and promoting the adhesivity of the uPA-uPAR complex (Higazi et al., 1995, J. Biol. Chem. 270:17375–17380; Higazi et al., 1996, Blood 87:3545–3549).

Binding of scuPA to uPAR enhances urokinase activity of scuPA (Higazi et al., 1995, J. Biol. Chem. 270:17375–17380). Formation of the scuPA-uPAR complex also dampens the capacity of PAI-1 to inhibit scuPA activity, relative to the capacity of PAI-1 to inhibit tcuPA activity (Higazi et al., 1996, Blood 87:3545–3549). Formation of a complex between scuPA and uPAR also alters the regulation of scuPA enzymatic activity by peptide substrates of plasmin and promotes binding of scuPA to vitronectin (Higazi et al., 1996, Thromb. Res. 84:243–252; Higazi et al., 1996, Blood 88:542–551; Wei et al., 1994, J. Biol. Chem. 269:32380–32388; Wei et al., 1996, Science 273:1551–1555; Deng et al., 1996, J. Cell Biol. 134:1563–1571; Stefansson et al., 1996, Nature 383:441–443; O'Reilly et al., 1996, Nature Med. 2:689–692).

A region of uPA, comprising the protein sequence RHRGGS (SEQ ID NO:1) at amino acid positions 179–184, is required for inhibition of uPA activity by PAI-1 (Madison et al., 1990, J. Biol. Chem. 265:21423–21426). Conservation of this sequence among mammalian uPA proteins has been demonstrated (Adams et al., 1981, J. Biol. Chem. 266:8476–8482). Working with a different plasminogen activator protein, namely tissue-type plasminogen activator (tPA), Madison et al. have identified a region of PAI-1 which is involved in inhibition of tPA by PAI-1 (1990, J. Biol. Chem. 265:21423–21426). This region of PAI-1 comprises the sequence RMAPEEIIMDR (SEQ ID NO:2) at amino acids 346–356. It has been postulated that electrostatic interactions between this region of PAI-1 and tPA play a role in stabilizing a tPA-PAI-1 complex. Similarly, it has been postulated that electrostatic interactions between a region of PAI-1 and uPA may contribute to formation of a PAI-1-uPA complex. It has been observed, however, that the scuPA-uPAR complex is less susceptible to inhibition by PAI-1 (Higazi et al., 1996, Blood 87:3545–3549) than is tcuPA or uPAR-bound tcuPA (Higazi et al., 1996, Blood 87:3545–3549; Ellis et al., 1990, J. Biol. Chem. 265:9904–9908).

In addition to inhibiting urokinase activity of uPA, PAI-1 also promotes the internalization and lysosomal degradation of uPA, which involves the $\alpha_2$-macroglobulin receptor/low density lipoprotein-related receptor protein ($\alpha_2$MR/LRP; Nykjaer et al., 1994, J. Biol. Chem. 269:25668–25676). The complex formed between PAI-1 and tcuPA binds to $\alpha_2$MR/LRP with considerably higher affinity than does either component alone. Although it has been demonstrated that the increased affinity of the complex results from an independent contribution of epitopes present in each ligand, a possible conformation-altering effect of PAI-1 upon uPA has not been excluded (Nykjaer et al., 1994, J. Biol. Chem. 269:25668–25676).

When scuPA is bound to uPAR, scuPA is protected from inactivation by PAI-1. Furthermore, binding of scuPA to uPAR inhibits binding of scuPA to $\alpha_2$MR/LRP and internalization of scuPA caused by such binding (Nykjaer et al., 1994, J. Biol. Chem. 269:25668–25676; Higazi et al., 1996, Blood 87:3545–3549). Two mechanisms have been postulated for the reduced affinity of uPAR-bound scuPA for $\alpha_2$MR/LRP. Nykjaer et al. (supra) proposed that the site at which scuPA contacts $\alpha_2$MR/LRP is shielded by uPAR. An alternative mechanism is that binding of scuPA to uPAR induces a conformational change that both promotes scuPA binding to integrin ligands and leads to a loss of the scuPA epitope recognized by $\alpha_2$MR/LRP (Higazi et al., 1996, Blood 88:542–551). The latter proposed mechanism is consistent with the observation that soluble scuPA has a higher affinity for $\alpha_2$MR/LRP than does tcuPA and with the observation that tcuPA loses affinity for $\alpha_2$MR/LRP when the active site of tcuPA is occupied by diisofluoryl phosphate (Nykjaer et al., 1994, J. Biol. Chem. 269:25668–25676).

scuPA bound to uPAR is active, protected from inactivation by PAI-1, and protected from clearance from the cell surface mediated by binding of scuPA to $\alpha_2$MR/LRP and subsequent degradation. Furthermore, scuPA that dissociates from uPAR reverts to an inactive conformation and becomes essentially insusceptible to inactivation by PAI-1. Thus, unbound scuPA retains the capacity to rebind to uPAR and revert once again to its active conformation.

There are abundant epidemiological data which indicate that the expression or uPA and uPAR in human tissue correlates with the conversion of cells from a benign to a neoplastic state. Furthermore, expression of uPA and uPAR is associated with a wide variety of common malignancies, and is predictive of future development of those malignancies. Interference with uPA activity by binding an antibody to uPA, by expression of an antisense oligonucleotide complementary to mRNA encoding uPA, or by overexpression of catalytically inactive forms of uPA impede tumor progression in several experimental murine models of human cancers (Ossowski, 1988, J. Cell Biol. 107:2437–2445; Ossowski et al., 1991, Canc. Res. 51:275–281; Kook et al., 1994, EMBO J. 13:3983–3991; Crowley et al., 1993, Proc. Natl. Acad. Sci. USA 90:5021–5025; Jankun et al., 1997, Canc. Res. 57:559–563).

The capacity to regulate uPA activity would enable the practitioner to regulate a number of important human diseases and symptoms thereof. There remains a significant unmet need for compositions useful for modulating the activity of uPA in a mammal, particularly in a human, and for methods of using those compositions to treat pathological conditions attributable to undesirable uPA activity in the mammal. Particularly needed are compositions and methods for promoting internalization and degradation of scuPA which act independently of activation of scuPA by plasmin, independently of binding of scuPA to uPAR, and independently of inactivation of soluble or uPAR-bound scuPA by PAI-1.

SUMMARY OF THE INVENTION

The invention includes a composition comprising a peptide having the amino acid sequence $X_1X_2X_3X_4X_5X_6X_7X_8$, wherein:

$X_1$ is hydrogen, an amino-terminal blocking group, or one to twenty amino acid. residues;

$X_2$ is an amino acid selected from the group consisting of D, E, H, K, and R;

$X_3$ is an amino acid selected from the group consisting of E and D;

$X_4$ is an amino acid selected from the group consisting of I, L, and V;

$X_5$ is an amino acid selected from the group consisting of I, L, and V;

$X_6$ is an amino acid selected from the group consisting of M;

$X_7$ is an amino acid selected from the group consisting of D, E, H, K, and R; and $X_8$ is hydrogen, a carboxyl-terminal blocking group, or one to twenty amino acid residues.

In one aspect, $X_1$ is hydrogen or an amino-terminal blocking group;

$X_2$ is an amino acid selected from the group consisting of D, E, and R;

$X_3$ is an amino acid selected from the group consisting of D and E;

$X_4$ is I;

$X_5$ is I;

$X_6$ is M;

$X_7$ is an amino acid selected from the group consisting of D and E; and $X_8$ is hydrogen or a carboxyl-terminal blocking group.

In a preferred embodiment, $X_1$ is hydrogen;

$X_2$ is E;

$X_3$ is E;

$X_4$ is I;

$X_5$ is I;

$X_6$ is M;

$X_7$ is D; and $X_8$ is hydrogen.

In another aspect, the composition of the invention further comprising a pharmaceutically acceptable carrier.

Also included in the invention is a method of affecting a biological process characterized by abnormal cell migration through a physiological barrier. The method comprises administering the composition of the invention to a mammal experiencing the biological process in an amount to affect the biological process.

In one aspect, the biological process is selected from the group consisting of angiogenesis, organogenesis, ovulation, inflammation, cancer, tumor cell invasion and metastasis, and atherosclerosis.

In a preferred embodiment, the mammal is a human.

The invention further includes a method of inhibiting PAI-1-dependent adhesion of a cell to a tissue of a mammal, the method comprising administering to the tissue the composition of the invention in an amount to inhibit adhesion of the cell to the tissue.

In one aspect, the tissue is in vivo in the mammal.

In a preferred embodiment, the mammal is a human.

Also included in the invention is a method of promoting clearance of scuPA from the surface of a mammalian cell, the method comprising administering the composition of claim 1 to the cell in an amount to promote clearance of the scuPA from the cell.

In one aspect, the cell is a human cell.

In a preferred embodiment, the composition is administered in vivo in the human.

Additionally, the invention includes a method of impeding pathological migration of a cell in a mammal. The method comprises administering to the mammal the composition of the invention in an amount effective to impede pathological migration of the cell.

In one aspect, the composition is administered to the mammal at the site of a tumor in the mammal.

In a preferred embodiment, the mammal is a human.

The invention yet further includes a method of inhibiting PAI-1 activity in a tissue of a mammal. The method comprises administering to the tissue the composition of the invention in an amount effective to inhibit PAI-1 activity in the tissue.

In a preferred embodiment, the mammal is a human.

In another preferred embodiment, the composition is administered in vivo in the human.

The invention also includes a kit comprising a peptide having the amino acid sequence $X_1X_2X_3X_4X_5X_6X_7X_8$, wherein:

$X_1$ is hydrogen, an amino-terminal blocking group, or one to twenty amino acid residues;

$X_2$ is an amino acid selected from the group consisting of D, E, H, K, and R;

$X_3$ is an amino acid selected from the group consisting of E and D;

$X_4$ is an amino acid selected from the group consisting of I, L, and V;

$X_5$ is an amino acid selected from the group consisting of I, L, and V;

$X_6$ is an amino acid selected from the group consisting of M;

$X_7$ is an amino acid selected from the group consisting of D, E, H, K, and R; and $X_8$ is hydrogen, a carboxyl-terminal blocking group, or one to twenty amino acid residues, and an instructional material for using the kit.

Also included is a composition comprising a combination of a peptide having the amino acid sequence $X_1X_2X_3X_4X_5X_6X_7X_8$, wherein:

$X_1$ is hydrogen, an amino-terminal blocking group, or one to twenty amino acid residues;

$X_2$ is an amino acid selected from the group consisting of D, E, H, K, and R;

$X_3$ is an amino acid selected from the group consisting of E and D;

$X_4$ is an amino acid selected from the group consisting of I, L, and V;

$X_5$ is an amino acid selected from the group consisting of I, L, and V;

$X_6$ is an amino acid selected from the group consisting of M;

$X_7$ is an amino acid selected from the group consisting of D, E, H, K, and R; and $X_8$ is hydrogen, a carboxyl-terminal blocking group, or one to twenty amino acid residues, and a thrombolytic agent.

In one aspect, the thrombolytic agent is selected from the group consisting of tissue plasminogen activator, streptokinase, urokinase, the streptokinase derivative and staphylokinase.

Further included in the invention is a composition comprising a combination of a peptide having the amino acid sequence $X_1X_2X_3X_4X_5X_6X_7X_8$, wherein:

$X_1$ is hydrogen, an amino-terminal blocking group, or one to twenty amino acid residues;

$X_2$ is an amino acid selected from the group consisting of D, E, H, K, and R;

$X_3$ is an amino acid selected from the group consisting of E and D;

$X_4$ is an amino acid selected from the group consisting of E, L, and V;

$X_5$ is an amino acid selected from the group consisting of I, L, and V;

$X_6$ is an amino acid selected from the group consisting of M;

$X_7$ is an amino acid selected from the group consisting of D, E, H, K, and R; and $X_8$ is hydrogen, a carboxyl-terminal blocking group, or one to twenty amino acid residues, and an anti-coagulating agent.

In one aspect, the anti-coagulating agent is selected from the group consisting of an agent which inhibits platelet function, and agent which inhibits the activity of thrombin, and agent which promotes the activity of activated protein kinase C, an anti-thrombin III agent, and a tissue factor pathway inhibitor.

BRIEF DESCRIPTION OF THE DRAWINGS

FIG. 1, comprising In FIG. 1A, the effect of the presence of the indicated peptide is shown, wherein "No Addition" means that none of the three peptides was added to the reaction mixture. In FIG. 1B, the effect of the presence of the indicated concentration of peptide EEIIMD is shown.

FIG. 4 is a graph which depicts the effect of the presence of peptide EEIIMD (SEQ ID NO: 3) on the activity of PAI-1.

FIG. 5, comprising

DETAILED DESCRIPTION

Figure 1A:
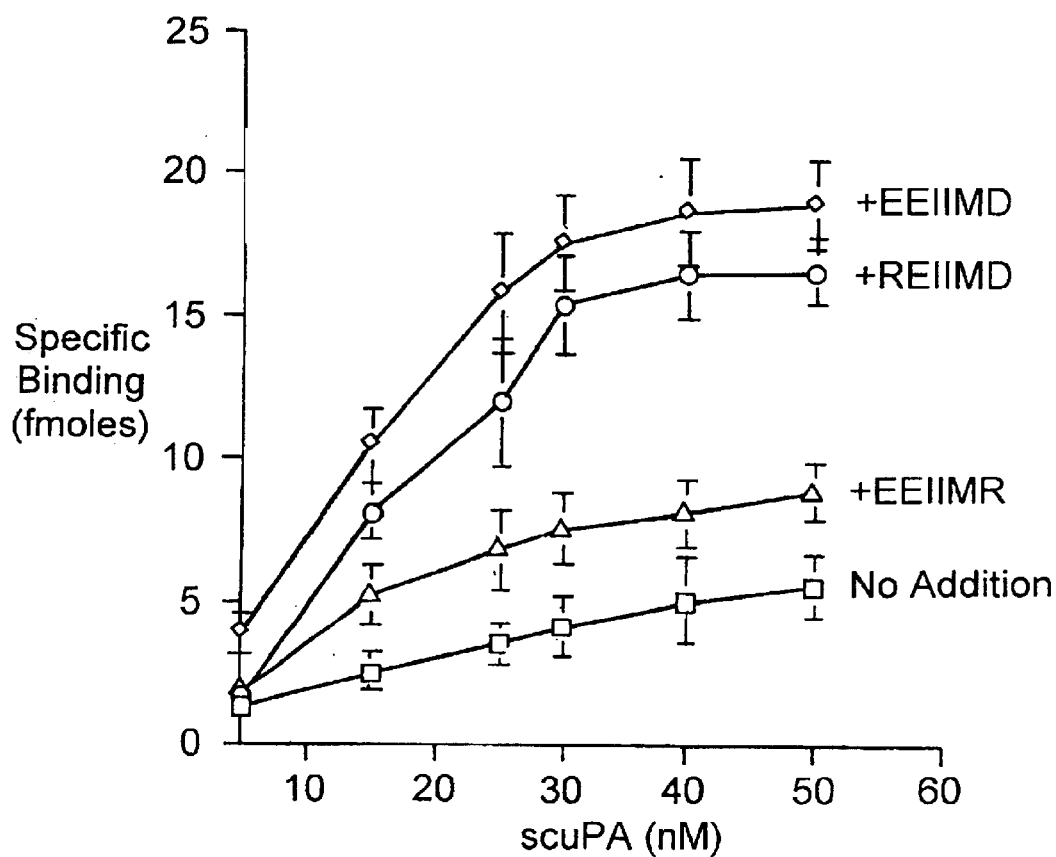
FIGS. 1A and 1B, is a pair of graphs which depict the effects which individual peptides had on binding of scuPA to LM-TK$^-$ cells ($\alpha$2MR$^+$/LRP, uPAR$^-$), wherein each individual peptide had a sequence selected from the group consisting of EEIIMD (SEQ ID NO:3), REIIMD (SEQ ID NO:4), and EEIIMR (SEQ ID NO:5).

The invention is based on the discovery of a peptide which promotes binding of scuPA to LM-TK$^-$ cells and thereby promotes internalization and degradation of scuPA by those cells. The peptide of the invention also promotes binding of scuPA to purified α2MR/LRP. Hence the peptide of the invention is useful for affecting the physiological availability of scuPA, and is thus useful for affecting biological processes characterized by abnormal cell migration through a physiological barrier, such biological processes including, but not being limited to, angiogenesis, organogenesis, ovulation, inflammation, cancer, tumor cell invasion and metastasis, and atherosclerosis.

Internalization and degradation of cell-associated uPA mediated by binding of uPA to α$_2$MR/LRP represents an important step in physiological control of plasmin formation. Complexes formed between tcuPA and PAI-1 are rapidly degraded. In contrast, the insusceptibility of scuPA to PAI-1 prevents clearance by PAI-1 inactivation prevents clearance of scuPA from cell surfaces from occurring to any appreciable degree. These observations suggest that α$_2$MR/LRP requires the presence of specific epitopes in scuPA for effective internalization and degradation thereof.

According to the data presented herein, the binding of scuPA to LM-TK$^-$ cells, which comprise α$_2$MR/LRP but lack uPAR, was stimulated by the presence in the extracellular medium of the hexapeptide, EEIIMD (SEQ ID NO:3). The presence of peptide EEIIMD increased the value of the B$_{max}$ constant for scuPA binding four-fold, and half-maximal effect was achieved at a peptide concentration of about 50 micromolar. B$_{max}$ represents the maximum number of binding sites of the surface of a cell at saturation. The magnitude of the increase in the maximum binding velocity was dependent on the charge of the C-terminal amino acid, but was not dependent on the charge of the N-terminal amino acid of the peptide.

Peptide EEIIMD (SEQ ID NO:3) promoted binding of scuPA to purified α$_2$MR/LRP. Peptide EEIIMD also accelerated the rate of internalization and degradation of scuPA by LM-TK$^-$ cells. Binding of scuPA to LM-TK$^-$ cells and internalization of scuPA by those cells in the presence of peptide EEIIMD were inhibited by the presence of either rRAP or an anti-α$_2$MR/LRP antibody. Peptide EEIIMD had no effect on binding of tcuPA to either LM-TK$^-$ cells or purified α$_2$MR/LRP, and did not affect scuPA-uPAR complex formation. Thus, peptide EEIIMD regulates binding of scuPA to α$_2$MR/LRP, and EEIIMD-promoted binding of scuPA to α$_2$MR/LRP represents a method of promoting internalization and degradation of scuPA by cells comprising α$_2$MR/LRP independently of both activation of scuPA by plasmin and binding of scuPA to uPAR. Promoting internalization and degradation of scuPA by cells inhibits biological processes characterized by abnormal cell migration through a physiological barrier The presence of cell-associated scuPA was regulated by exposing LM-TK$^-$ cells to peptide EEIIMD, the sequence (SEQ ID NO:3) of which is homologous with a portion of the amino acid sequence of PAI-1, being amino acids 350–355 of PAI-1. Peptide EEIIMD was observed to be a competitive inhibitor of PAI-1 binding to tcuPA. This peptide also bound to scuPA under experimental conditions under which PAI-1 did not bind to scuPA. It was furthermore observed that peptide EEIIMD promoted internalization and degradation of scuPA by means of binding of scuPA to cellular α$_2$MR/LRP.

Thus, the peptide of the invention as described herein including, but not limited to, peptide EEIIMD (SEQ ID NO:3) and peptides and peptidomimetics derived therefrom, may be used to promote clearance of scuPA from cell surfaces, thereby impeding pathologic cell migration. In addition, the peptide of the invention may be used synergistically with inhibitors of uPA-uPAR complex formation. Inhibitors of uPA-uPAR complex formation are known in the art and include those that are peptide- or antibody-based, those which are directed to the binding sequences in either uPA or uPAR, those based on sequences from other proteins believed to interact with the uPA-uPAR complex, organic inhibitors, antisense-based inhibitors, and the like. For example, Suramin may be used to inhibit complex formation. When inhibitors of uPA-uPAR complex formation are used alone in a subject experiencing a biological process characterized by abnormal cell migration through a physiological barrier, a biologically relevant amount of scuPA remains bound to uPAR or in the cellular environment near uPAR. A biologically relevant amount of scuPA may furthermore be capable of binding to uPAR owing to persistent local synthesis of scuPA. A biologically relevant amount of scuPA means an amount of scuPA which is capable of influencing the migration of a cell through a physiological barrier. Thus, use of an inhibitor of uPA-uPAR complex formation alone is insufficient to result in complete clearance of scuPA from a cell surface, such that a biologically relevant amount of scuPA does not remain on the cell surface.

A peptide of the invention, when used alone or in combination with an inhibitor of uPA-uPAR complex formation, may be used to efficiently promote clearance of scuPA from cell surfaces. When a peptide of the invention and an inhibitor of uPA-uPAR complex formation are used in combination, a synergistic effect results, the peptide of the invention causing internalization of scuPA by means of scuPA binding to α$_2$MR/LRP and subsequent internalization and degradation of scuPA, and the uPA-uPAR binding inhibitor preventing sequestration of a biologically relevant amount of scuPA bound to uPAR.

The peptide of the invention including, but not limited to, peptide EEIIMD (SEQ ID NO:3) is also useful as an inhibitor of PAI-1 activity. There is abundant human epidemiologic and experimental data which link PAI-1 activity with thrombosis. As one example, arterial clots are relatively resistant to thrombolytic agents, in part because thrombin binding to fibrin promotes the release of PAI-1 by activated platelets which become trapped in the fibrin meshwork. Another important recent observation is that PAI-1 regulates cell adhesion mediated by the uPA-uPAR complex. The peptide of the invention including, but not limited to peptide EEIIMD and peptides and peptidomimetics derived therefrom, is a competitive inhibitor of PAI-1-binding to scuPA and to tcuPA. The presence of the peptide of the invention in the extracellular milieu inhibits cleavage of cell-surface scuPA by PAI-1 by removing scuPA so that it cannot be converted to tcuPA. Thus, the peptide of the invention promotes endogenous thrombolysis, reducing the risk of thrombosis in a mammal. Promotion of endogenous thrombolysis is a useful therapeutic and prophylactic treatment of individual subjects afflicted with a wide variety of diseases and disorders involving thrombogenesis. Such diseases and disorders include, but are not limited to, heart attack, stroke, deep venous thrombosis, pulmonary embolus, and the presence in an individual of an abnormally large amount of PAI-1. The subject may be any mammal, and is preferably a human subject.

The peptide of the invention may be used alone or in combination with known thrombolytic agents, thereby permitting the use of far lower and safer concentrations of known thrombolytic agents. Known thrombolytic agents include, by way of example, tissue plasminogen activator, streptokinase, urokinase, the streptokinase derivative APSAC, and staphylokinase.

The peptide of the invention may also be used synergistically with known anticoagulants. The anticoagulants with which the peptide of the invention may be used include, but are not limited to, those which inhibit platelet function, those which inhibit the activity of thrombin, those which promote the activity of, for example, activated protein kinase C, anti-thrombin III, a tissue factor pathway inhibitor, and the like. Combined use of the peptide of the invention with a known anticoagulant is effective to prevent thrombus formation and to promote thrombolysis of existing clots.

The peptide of the invention may be used to inhibit PAI-1-dependent cell adhesion, a critical control point during cell migration through tissues. Thus, the peptide of the invention may be used to inhibit angiogenesis, metastasis, the ingrowth of smooth muscle cells into atherosclerotic plaques, infiltration of leukocytes into inflamed or damaged tissue, ovulation, binding of spermatozoa to ova, placental development, and other types of cell migration, particularly undesirable cell migration.

| Table of Abbreviations Used Herein | |
|---|---|
| uPA | urokinase-type plasminogen activator |
| scuPA | single chain urokinase-type plasminogen activator |
| tcuPA | two chain urokinase-type plasminogen activator |
| uPAR | urokinase-type plasminogen activator receptor |
| suPAR | soluble urokinase-type plasminogen activator receptor |
| tPA | tissue-type plasminogen activator |
| PAI-1 | plasminogen activator inhibitor-1 |
| $\alpha_2$MR/LRP | $\alpha_2$-macroglobulin receptor/low density lipoprotein-related receptor protein |
| rRAP | recombinant 39 kilodalton $\alpha_2$MR/LRP. |
| PBS | phosphate-buffered saline |
| TBS | Tris-chloride buffered saline |
| DMEM | Dulbecco's Modified Eagle's Medium |
| BSA | bovine serum albumin. |

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |

| -continued | | |
|---|---|---|
| Full Name | Three-Letter Code | One-Letter Code |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The present invention also provides for analogs of the peptides described herein. Analogs can differ from the peptides described herein by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine; and phenylalanine, tyrosine.

Modifications which do not alter the primary sequence of the peptide of the invention may be used in the compositions and methods described herein. Modifications which do not normally alter primary sequence include in vivo, or in vitro chemical derivativization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzmes. Also embraced are sequences which have phosphorylated amino acid residues, e.g., phosphotyrosine, phosphoserine, or phosphothreonine.

Also included are polypeptides which have been modified using ordinary chemical or molecular biological techniques so as to improve their resistance to proteolytic degradation or to optimize solubility properties or to render them more suitable as a pharmaceutical agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The peptide of the invention has the general formula $$X_1X_2X_3X_4X_5X_6X_7X_8$$

wherein:

$X_1$ is hydrogen, an amino-terminal blocking group, or one to twenty amino acid residues;

$X_2$ is an amino acid selected from the group consisting of D, E, H, K, and R;

$X_3$ is an amino acid selected from the group consisting of E and D;

$X_4$ is an amino acid selected from the group consisting of I, L, and V;

$X_5$ is an amino acid selected from the group consisting of I, L, and V;

$X_6$ is an amino acid selected from the group consisting of M;

$X_7$ is an amino acid selected from the group consisting of D, E, H, K, and R; and $X_8$ is hydrogen, a carboxyl-terminal blocking group, or one to twenty amino acid residues.

Preferably, $X_1$ is hydrogen or an amino-terminal blocking group, $X_2$ is an amino acid selected from the group consisting of D, E, and R, $X_3$ is an amino acid selected from the group consisting of D and E, $X_4$ is I, $X_5$ is I, $X_6$ is M, $X_7$ is an amino acid selected from the group consisting of D and E, and $X_8$ is hydrogen or a carboxyl-terminal blocking group. More preferably, $X_1$ is hydrogen, $X_2$ is E, $X_3$ is E, $X_4$ is I, $X_5$ is I, $X_6$ is M, $X_7$ is D, and $X_8$ is hydrogen.

Most preferably, the peptide of the invention is EEIIMD.

The peptide of the invention is also referred to herein as the "PAI-1" peptide.

The invention encompasses the preparation and use of pharmaceutical compositions comprising the peptide of the invention as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. Administration of one of these pharmaceutical compositions to a subject is useful for treating a variety of diseases or disorders as described elsewhere herein. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, in asal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet-comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para- hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985*, Remington's Pharmaceutical Sciences*, Mack Publishing Co., Easton, Pa., which is incorporated herein by reference.

Typically dosages of the peptide of the invention which may be administered to an animal, preferably a human, range in amount from 1 $\mu$g to about 100 g per killogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per killogram of body weight of the animal. More preferably, the dosage will vary from about 10 mg to about 1 g per killogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising the peptide of the invention and an instructional material which describes adventitially administering the peptide to a cell or a tissue of a mammal. In another embodiment, this kit comprises a (preferably sterile) solvent suitable for dissolving or suspending the peptide of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains peptide of the invention or be shipped together with a container which contains the peptide. Alternatively, the instructional material may be shipped separately from the container with the intention that the instructional material and the compound be used cooperatively by the recipient.

The invention is now described with reference to the following experimental details. The experimental details are provided for the purpose of illustration only and the invention should in no way be construed as being limited to the embodiments described herein, but rather should be construed to encompass any and all variations which become evident as a result of the teaching provided herein.

EXAMPLE 1

Regulation of scuPA by the Peptide of the Invention

To examine the mechanism by which uPA binds to $\alpha_2$MR/LRP, the effect of the presence of peptide EEIIMD (SEQ ID NO: 3) on the cellular binding, interalization, and degradation of scuPA, the scuPA-suPAR complex, and tcuPA was examined. The peptide increased recognition of scuPA, but not tcuPA, by $\alpha_2$MR/LRP. The data indicate that interaction of scuPA with a portion of PAI-1, results in a conformational change of scuPA that modulates the activity thereof. The peptide of the invention was discovered to promote internalization and degradation of scuPA by cells which express $\alpha_2$MR/LRP.

The materials and methods used in the experiments of this Example are now described.

Recombinant scuPA and recombinant suPAR were purified as reported and were obtained from Abbott Laboratories (Abbott Park, Ill.; Higazi et al., 1996, Blood 87:3545–3549; Higazi et al., 1997, J. Biol. Chem. 272:5348–5353). Peptides EEIIMD (SEQ ID NO: 3), REIIMD (SEQ ID NO: 4), and EEIIMR (SEQ ID NO: 5) were synthesized using methods well known in the art of peptide synthesis. Glu-plasminogen, tcuPA, PAI-1, and the plasmin chromogenic substrate Spectrazyme PLT were obtained from American Diagnostica, Inc. (Greenwich, Conn.). Purified $\alpha_2$MR/LRP and rRAP were prepared as described (Williams et al., 1992, J. Biol. Chem. 267:9035–9040). The LM-TK$^-$ cell line was obtained from the American Type Tissue Collection (catalog number CCL 1.3 L-M(TK$^-$) Rockville, Md.). scuPA, suPAR, and tcuPA were radiolabeled with $^{125}$I as described (Bamathan et al., 1990, J. Biol. Chem. 265:2865–2872) using iodobeads obtained from the Pierce Chemical Company (Rockford, Ill.).

Preparation of Protein Complexes

To prepare the scuPA-suPAR complex, suPAR and scuPA were incubated together at a molar ratio of 1.25 to 1, respectively, for one hour at 37° C. at ten times the desired final concentration in binding buffer (comprising PBS supplemented with 1.5% (w/v) BSA).

To form complexes with PAI-1, PAI-1 was added to a solution comprising binding buffer and scuPA, tcuPA, the scuPA/suPAR complex, or the tcuPA/suPAR complex at a 1:1 molar ratio, and the solution was incubated for thirty minutes at 37° C.

Protein complexes were diluted to a desired working concentration immediately before use.

Assessment of Plasminogen Activator Activity

A solution comprising 5 nanomolar tcuPA, 0 or 200 micromolar peptide EEIIMD (SEQ ID NO:3), and 0 or 200 micromolar peptide REIIMD (SEQ ID NO:4) was incubated for thirty minutes. The solution was then added to a reaction mixture comprising 25 nanomolar PAI-1, 50 nanomolar Glu-plasminogen, and 50 micromolar chromogenic substrate, and the optical density of the mixture at 405 nanometers was measured continuously, as described (Higazi et al., 1996, Blood 87:3545–3549).

Lipand Binding Assays

Binding of radiolabeled ligands, including scuPA and tcuPA, to cells was measured as described (Higazi et al., 1996, Blood 88:542–551). Briefly, LM-TK$^-$ cells were suspended in DMEM (GIBCO, Grand Island, N.Y.) containing 10% (v/v) fetal calf serum and were grown to confluence at 37° C. overnight in 96-well Falcon™ multiwell tissue culture dishes (Becton Dickinson, Lincoln Park, N.J.). The cells were chilled for one hour on ice and were washed twice with chilled binding buffer. $^{125}$I-labeled ligands, with or without 50-fold molar excess of non-labeled ligands, were added to the cells in the presence or absence of 0–300 micromolar peptide, and the cell cultures were incubated for two hours at 4° C. The cells were washed four times with binding buffer, solubilized in 0.1 N NaOH, and the cell extract was assessed for radioactivity. In other experiments, binding of labeled ligands was performed in the absence or presence of 400 nanomolar rRAP diluted in TBS containing 4 millimolar $Ca^{2+}$, or in the presence of 100 micrograms per milliliter affinity purified IgG anti-$\alpha_2$MR/LRP antibody. Assays were repeated at least three times, and data presented herein represent the mean and standard deviation.

Solid Phase Bindings Assay

To measure the binding of labeled ligands to $\alpha_2$MR/LRP, a 96-well microtiter plate was incubated with 3 micrograms per milliliter purified $\alpha_2$MR/LRP or with 3 micrograms per milliliter BSA in TBS containing 4 millimolar $Ca^{2+}$ overnight at 4° C. The buffer was removed, and the non-reacted sites on the plate were blocked using a blocking solution comprising TBS, 4 millimolar $Ca^{2+}$, 0.05% (v/v) Tween-20, and 3% (w/v) BSA. The wells of the plate were filled with the blocking solution and incubated for one hour at 4° C. Next, the blocking solution was removed, each well was filled with a solution comprising blocking solution and 0 or 200 nanomolar rRAP, and the plate was incubated at 4° C. for another hour. Binding of $^{125}$I-labeled ligands to immobilized $\alpha_2$MR/LRP was determined as described (Higazi et al., 1996, Blood 88:542–551; Nykjaer et al., 1993, J. Biol. Chem. 268:15048–15055).

Assessment of Internalization and Degradation of scuPA by LM-TK$^-$ Cells

LM-TK$^-$ cells were grown overnight at 37° C. to confluence in 48-well Falcon™ Multiwell tissue culture dishes (Becton Dickinson, Lincoln Park, N.J.). Cells were prechilled on ice for one hour, washed twice with a buffer comprising TBS, 4 millimolar $Ca^{2+}$, and 3% (w/v) BSA, and incubated for one hour at room temperature with the same buffer or with buffer supplemented with either 400 nanomolar rRAP or 100 micrograms per milliliter IgG anti-$\alpha_2$MR/LRP. The buffer was removed, 125I-scuPA was added to the cells, and the cells were incubated for two hours at 4° C. in the presence of 0–300 micromolar peptide, 0 or 400 nanomolar rRAP, and 0 or 100 micrograms per milliliter anti-$\alpha_2$MR/LRP. Unbound ligand was removed and cells were washed five times with the buffer. DMEM comprising 4 millimolar $Ca^{2+}$, 0 or 400 nanomolar rRAP, and 0 or 100 micrograms per milliliter anti-$\alpha_2$MR/LRP was added to the cells, and the cells were incubated for eighteen hours at 37° C. Internalization and degradation of scuPA were measured as described (Kounnas et al., 1993, J. Biol. Chem. 268:21862–21867; Li et al., 1994, J. Biol. Chem. 269:8153–8158). Briefly, to measure internalization, cells were washed twice with the buffer, a solution comprising 50 millimolar glycine 150 millimolar NaCl at pH 3.0 was added to the cells, and the cells were incubated for fifteen minutes at 4° C. to dissociate cell surface-bound ligands. Cells were solubilized by adding 0.1 N NaOH to the cell-containing solution and incubating the solution for ten minutes. Radioactivity in the cell extract was assessed. To measure scuPA degradation, the medium was removed from each cell culture after the eighteen hour incubation period, trichloroacetic acid was added to a final concentration of 10% (v/v), precipitated protein was separated by centrifugation, and radioactivity in the supernatant was assessed.

The results of the experiments presented in this Example are now described.

Figure 1B:
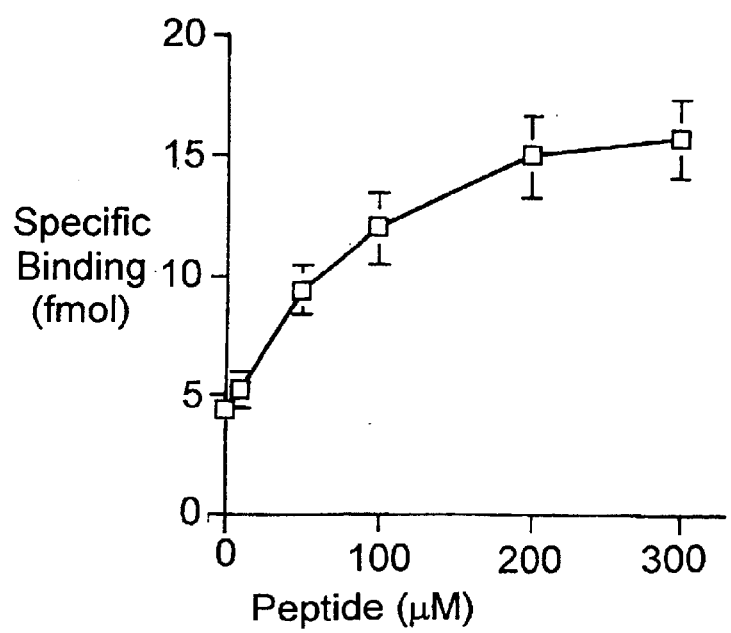

Peptide EEIIMD (SEQ ID NO: 3) promoted binding of scuPA to LM-TK$^-$ cells. The data presented herein in FIG. 1A indicate that only a minimal amount of scuPA bound to LM-TK$^-$ cells, consistent with a previous report (Higazi et al., 1996, Blood 88:542–551) when scuPA was present in the extracellular medium. Binding of scuPA to these cells was promoted by the presence of peptide EEIIMD in a dose-dependent and saturable manner, both with respect to scuPA concentration, as depicted in FIG. 1A, and with respect to peptide concentration, as depicted in FIG. 1B.

Promotion of scuPA binding to LM-TK$^-$ cells was evident at all concentrations of scuPA tested, and the increase in scuPA binding in the presence of peptide EEIIMD (SEQ ID NO: 3) was primarily the result of a four-fold increase in the value of Bmax. Using Scatchard analysis, it was determined that little specific binding of scuPA to LM-TK$^-$ cells occurred in the absence of peptide EEIIMD, the value of $K_d$ for scuPA being greater than one micromolar in the absence of the peptide. In contrast, the value of $K_d$ for scuPA in the presence of the peptide was approximately 35 nanomolar. Half maximal stimulation of scuPA binding to LM-TK⁻ cells was achieved using a peptide EEIIMD concentration equal to approximately 50 micromolar, the near-maximal effect being observed using approximately 300 micromolar peptide, as depicted in FIG. 1B.

Studies were performed to identify the sequence requirements of the peptide of the invention involved in stimulation of scuPA binding to LM-TK⁻ cells. Peptide EEIIMD (SEQ Id NO: 3) was the lead compound in these investigations. Two peptides, having amino acid sequences REIIMD (SEQ ID NO:4) and EEIIMR, were prepared, and the effect of the presence of these peptides on the binding of scuPA to LM-TK⁻ cells was investigated, analogously to the investigations of the effect of the presence of EEIIMD described herein. As depicted in FIG. 1A, it was found that peptide REIIMD was nearly as potent a promoter of scuPA binding to LM-TK⁻ cells as was peptide EEIIMD. In contrast, peptide EEIIMR exhibited approximately 20% of the scuPA-binding-promoting activity exhibited by peptide EEIIMD.

Hence, it is apparent that the charge of the amino acid residue at the amino terminus of peptide EEIIMD (SEQ ID NO: 3) is not important. Substitution of this Glu residue by Arg has been demonstrated to result in a peptide which is an effective promoter of scuPA binding to LM-TK⁻ cells. Therefore, the amino terminal Glu residue of peptide EEIIMD may be substituted with Arg, His, Lys, or Asp to generate peptides which are included in the invention. Thus, peptides having the general formula XEIIMD may be used as effective promoters of scuPA binding to LM-TK⁻ cells, wherein X is an amino acid residue selected from the group consisting of D, E, H, K, and R. Preferably, X is D, E, or R. Also preferably, X is D or E. Most preferably, X is E.

Furthermore, it is apparent that the charge of the amino acid residue at the carboxyl terminus of peptide EEIIMD (SEQ ID NO:3) is import to the magnitude, but not to the existence of the capacity of the peptide to promote scuPA binding to LM-TK⁻ cells. It has been demonstrated herein that if the carboxyl terminal amino acid residue has a positive charge, the peptide will have a reduced, but non-negligible, capacity to promote scuPA binding to LM-TK⁻ cells, relative to peptide EEIIMD. Thus, peptides having the general formula EEIIMD are included in the invention and may be used as effective promoters of scuPA binding to LM-TK⁻ cells, wherein Z is an amino acid residue selected from the group consisting of D, E, H, K, and R. Preferably, Z is D, E, or R. Also preferably, Z is D or E. Most preferably, Z is E.

It has been reported that substitution of the glutamic acid residue at amino acid position 350 of PAI-1 with an arginine residue does not affect the capacity of PAI-1 to inhibit the proteolytic activity of tPA, and that substitution of the aspartic acid residue at amino acid position 355 of PAI-1 with an arginine residue prevents PAI-1 from inhibiting the proteolytic activity of tPA (Madison et al., 1990, J. Biol. Chem. 265:21423–21426). The report of Madison et al. is consistent with the results described herein, even though Madison et al. studied the interaction of PAI-1 with a different protein, namely tPA, and used full-length PAI-1 protein, rather than the novel peptide of the invention.

Figure 2:
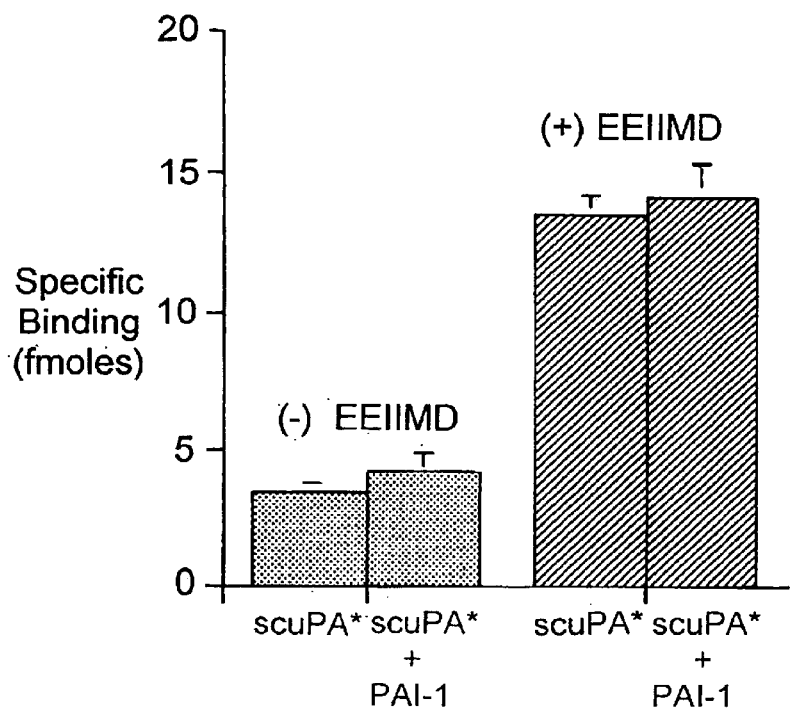
FIG. 2 is a bar graph which depicts the effect of peptide EEIIMD on binding of the scuPA in the presence or absence of PAI-1 to LM-TK$^-$ cells.
Figure 3:
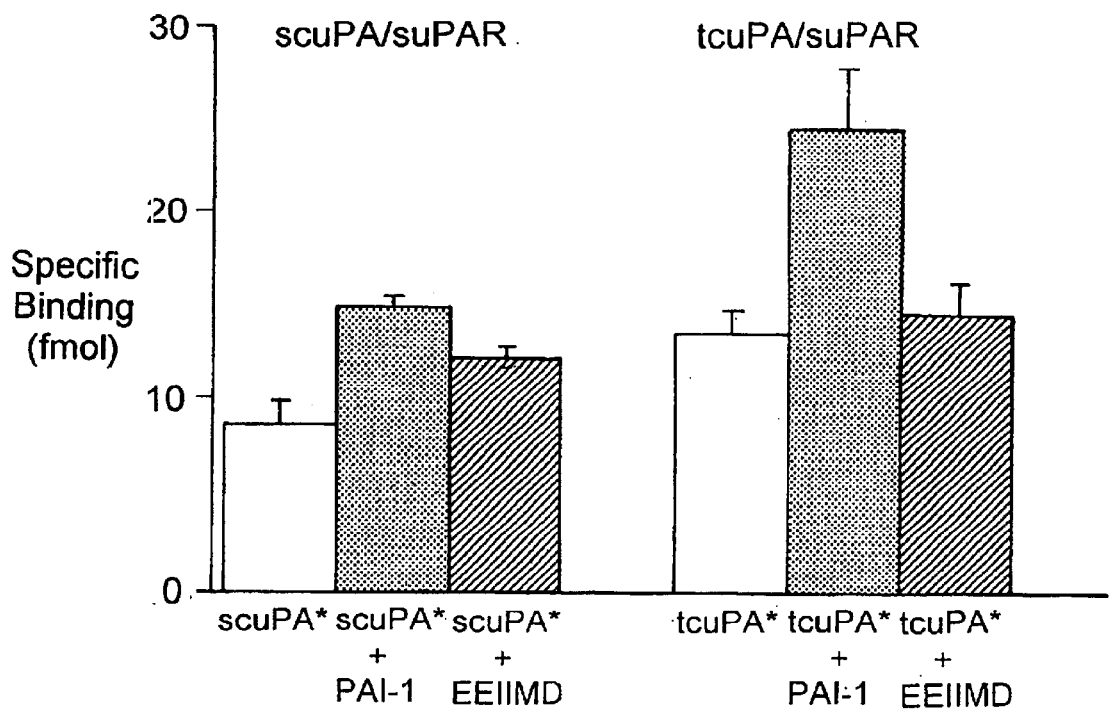
FIG. 3 is a bar graph which depicts the effect of PAI-1 and the effect of peptide EEIIMD (SEQ ID NO:3) on the binding of the scuPA-suPAR and the tcuPA-suPAR complexes to LM-TK$^-$ cells.

The effect of the presence of peptide EEIIMD (SEQ ID NO:3) on binding of scuPA to LM-TK⁻ cells in the presence of PAI-1 was examined. Preincubation of scuPA with PAI-1 prior to addition of peptide EEIIMD minimally increased binding of $^{125}$I-scuPA to LM-TK⁻ cells, as depicted in FIG. 2. This observation is consistent with the low affinity of PAI-1 for scuPA that has been reported (Kruithof, 1988, Enzyme 40:113–121; Lijnen et al., 1994, Eur. J. Biochem. 224:567–574; Kruithof et al., 1984, Blood 64:907–913; Andreasen et al., 1986, J. Biol. Chem. 261:7644–7651; Manchanda et al., 1995, J. Biol. Chem. 270:20032–20035). The scuPA-binding-promoting effect of peptide EEIIMD in the presence of PAI-1 was identical to the effect observed in the absence of PAI-1. Hence, it is clear that PAI-1 did not displace the peptide from The effect of PAI-1 and peptide EEIIMD (SEQ ID NO:3) on the binding of the scuPA-suPAR complex and of tcuPA to LM-TK⁻ cells was examined. As depicted in FIG. 3, the presences of PAI-1 and peptide EEIIMD each caused a minimal increase in binding of the scuPA-suPAR complex to LM-TK⁻ cells. PAI-1 clearly stimulated binding of tcuPA, as reported by others (Nykjaer et al., 1994, J. Biol. Chem. 269:25668–25676; Nykjaer et al., 1992,J. Biol. Chem. 267:14543–14546). In contrast, as depicted in FIG. 3, peptide EEIIMD had no effect on binding of the tcuPA-suPAR complex to LM-TK⁻ cells. The presence of peptide EEIIMD also failed to stimulate binding of tcuPA to LM-TK⁻ cells. The failure of peptide EEIIMD to stimulate binding of tcuPA or the tcuPA-suPAR complex to LM-TK⁻ or to more than minimally stimulate binding of the scuPA-suPAR complex to LM-TK⁻ cells likely results from either the inability of the peptide to bind to the site of the scuPA protein to which PAI-1 binds or the conformational state of scuPA. To address the question of whether peptide EEIIMD can bind to the site of the uPA protein to which PAI-1 binds, the capacity of the peptide to competitively inhibit PAI-1 activity was assessed using tcuPA as the substrate of PAI-1. The data depicted in FIG. 4 indicate that peptide EEIIMD inhibits PAI-1 activity. The control peptide EEIIMR did not inhibit PAI-1 activity. Hence, peptide EEIIMD and PAI-1 appear to interact with at least one common portion of scuPA.

It is understood that complexes between tcuPA and PAI-1 are internalized and degraded following binding of the tcuPA-PAI-1 complex to $\alpha_2$MR/LRP (Li et al., 1994, J. Biol. Chem. 269:8153–8158; Nykjaer et al., 1992, J. Biol. Chem. 267:14543–14546). Investigations were performed to determine whether the presence of peptide EEIIMD increased the binding, internalization, and degradation of scuPA through this pathway.

Figure 5A:
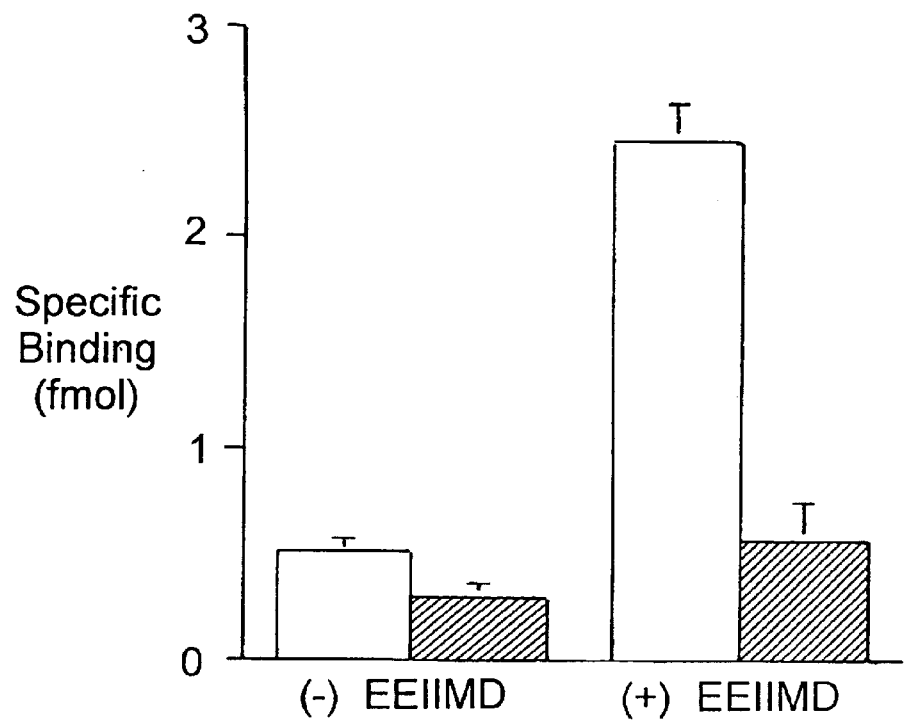
FIGS. 5A and 5B, is a pair of bar graphs which depict the effects of the presence of peptide EEIIMD (SEQ ID NO: 3) on binding of scuPA to $\alpha_2$MR/LRP and to LM-TK$^-$ cells. The results depicted in FIG. 5A were obtained by assessing binding of labeled scuPA to purified $\alpha_2$MR/LRP in the absence or presence of rRAP and in the absence or presence of the peptide. Open boxes represent data collected in the absence of rRAP, and striped boxes represent data collected in the presence of rRAP. The data depicted in FIG. 5B were obtained by assessing binding of labeled scuPA to LM-TK$^-$ cells in the absence or presence of the peptide. Data representing binding in the presence of 4 millimolar Ca$^{2+}$ are represented by open boxes. Data representing binding in the presence of 400 nanomolar rRAP are indicated by grey boxes. Data representing binding in the presence of 100 micrograms/milliliter anti-$\alpha_2$MR/LRP IgG are indicated by black boxes.
Figure 5B:
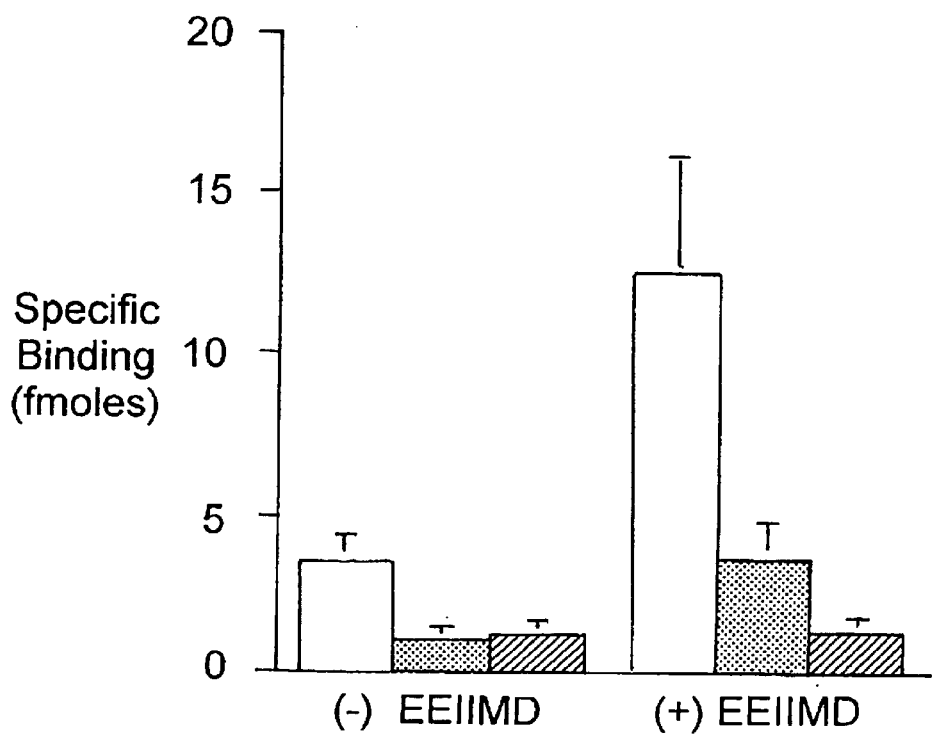
Figure 6:
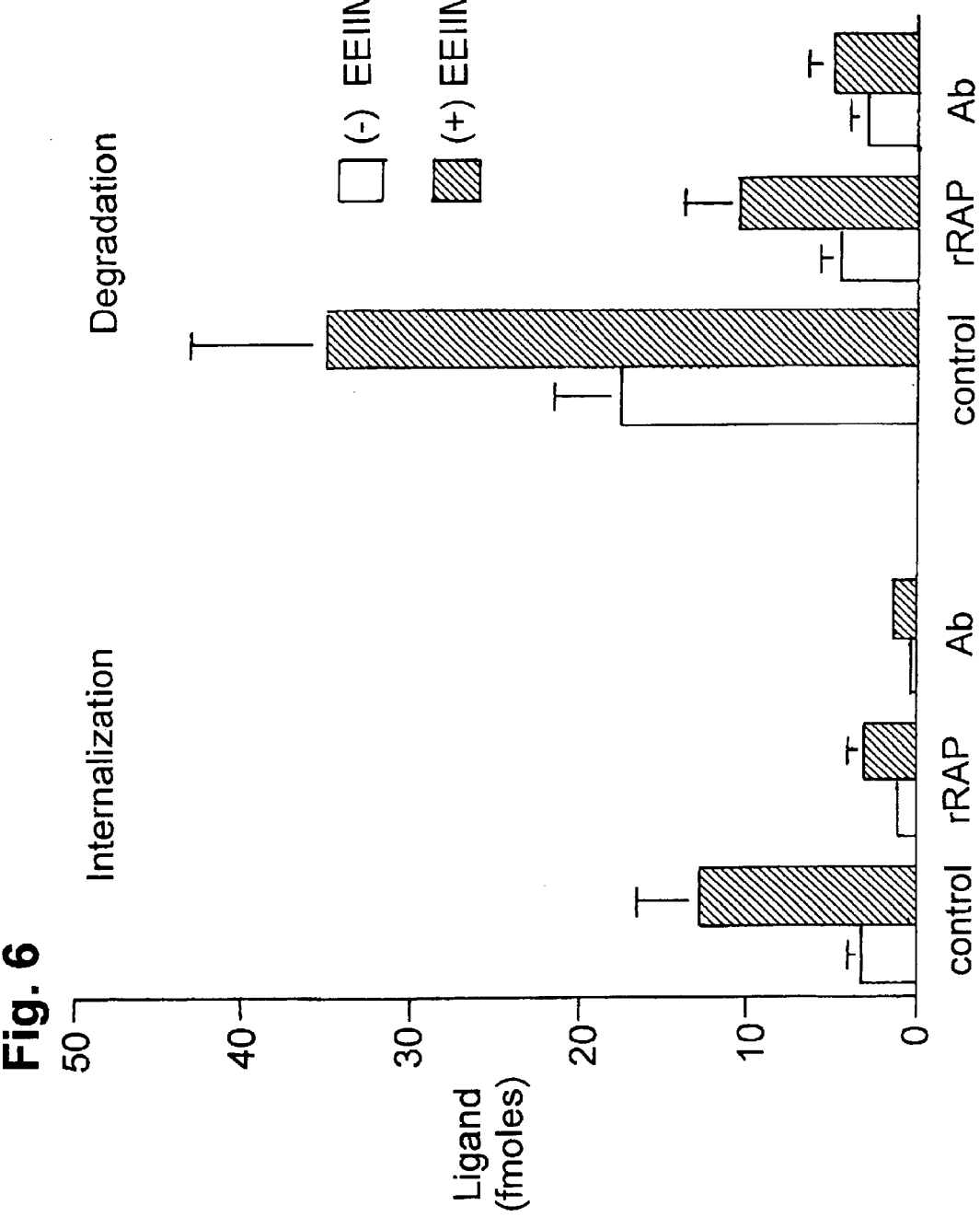
FIG. 6 is a bar graph which depicts the effect of the presence of peptide EEIIMD (SEQ ID NO: 3) on the internalization and degradation of scuPA by LM-TK$^-$ cells. "Control" refers to data collected in experiments wherein cells were incubated in the absence of rRAP and anti-$\alpha_2$MR/LRP. "rRAP" refers to data collected in experiments wherein cells were incubated in the presence of rRAP. "Ab" refers to data collected in experiments wherein cells were incubated in the presence of an anti-$\alpha_2$MR/LRP antibody. Data collected in experiments performed in the absence of the peptide are indicated by open boxes. Data collected in experiments performed in the presence of the peptide are indicated by striped boxes.

Peptide EEIIMD (SEQ ID NO:3) promoted binding of scuPA to purified $\alpha_2$MR/LRP, and the promoting effect of peptide EEIIMD was inhibited by the presence rRAP, as depicted in FIG. 5A. In addition, promotion by peptide EEIIMD of binding of scupA to LM-TK⁻ cells was inhibited approximately 70% by the presence of 400 nanomolar rRAP and approximately 85% by the presence of affinity purified anti-$\alpha_2$MR/LRP IgG, as depicted in FIG. 5B. Furthermore, EEIIMD promoted both internalization and degradation of scuPA by LM-TK⁻ cells, as depicted in FIG. 6. Promotion of scuPA internalization and degradation by LM-TK⁻ cells was inhibited approximately 70% by the presence of 400 nanomolar rRAP and approximately 80% by the presence 100 micrograms per milliliter of anti-$\alpha_2$MR/LRP IgG.

Although it has been postulated that binding of the tcuPA-PAI-1 complex to $\alpha_2$MR/LRP is mediated by independent epitopes in tcuPA and $\alpha_2$MR/LRP (Nykjaer et al., 1994, J. Biol. Chem. 269:25668–25676), such a mechanism does not explain the stimulatory effect of the presence of peptide EEIIMD (SEQ ID NO: 3) on scuPA binding to $\alpha_2$MR/LRP which has been described herein. The peptide of the invention is not large enough to affect both scuPA and $\alpha_2$MR/LRP simultaneously. Furthermore, peptide EEIIMD bound to tcuPA, as shown by inhibition of PAI-1 activity, but did not increase tcuPA binding to $\alpha_2$MR/LRP. Therefore, the observation that the presence of peptide EEIIMD increased the value of $B_{max}$ for binding of scuPA to $\alpha_2$MR/LRP suggests that the peptide induces a previously unrecognized alteration in the secondary structure of scuPA, relative the conformational state of the native molecule, that is specifically recognized by $\alpha_2$MR/LRP. Put another way, the results described herein suggest that the site on the scuPA protein to which peptide EEIIMD binds functions as an "allosteric" site. Consistent with this notion, the presence of peptide EEIIMD stimulated binding of scuPA to $\alpha_2$MR/LRP, but had no effect on binding of either the scuPA-suPAR complex or tcuPA to $\alpha_2$MR/LRP. These results are consistent with the reported differences in the ability of scuPA, the scuPA-suPAR complex and tcuPA to interact with $\alpha_2$MR/LRP (Nykjaer et al., 1994, J. Biol. Chem. 269:25668–25676).

It is likely that peptide EEIIMD (SEQ ID NO: 3) fails to stimulate cellular binding of tcuPA, even though this peptide binds to tcuPA, because the binding of peptide EEIIMD to tcuPA does not induce tcuPA to assume a secondary structure including the site recognized by $\alpha_2$MR/LRP. A similar mechanism may also account for the failure of peptide EEIIMD to induce cellular binding of the scuPA-suPAR complex to $\alpha_2$MR/LRP. Alternatively, the binding site for $\alpha_2$MR/LRP on scuPA may be induced and shielded by uPAR, consistent with the capacity of uPAR to block interaction of scuPA and the tcuPA-PAI-1 complex with $\alpha_2$MR/LRP (Nykjaer et al., 1994, J. Biol. Chem. 269:25668–25676; Higazi et al., 1996, Blood 88:542–551). Thus, conversion of scuPA to tcuPA is associated with the loss of the ability of peptide EEIIMD to induce the structure recognized by $\alpha_2$MR/LRP, presumably as a result of the loss of coordinate interaction between different portions of the molecule. Support for this interpretation comes from the observations that uPAR has little or no effect on the enzymatic activity of tcuPA (Higazi et al., 1995, J. Biol. Chem. 270:17375–17380) or on its susceptibility to inactivation by PAI-1 (Higazi et al., 1995, J. Biol. Chem. 270:17375–17380; Ellis et al., 1990, J. Biol. Chem. 265:9904–9908). These results provide additional support for the idea that the conversion of scuPA to tcuPA is the first step in the inactivation and degradation of scuPA.

Irrespective of the sequence of events, the capacity of the presence of peptide EEIIMD (SEQ ID NO: 3) to stimulate cellular binding of scuPA provides additional support for the notion that the physiological activity of scuPA can be regulated by altering its conformation, as a result of which internalization and degradation of the protein is accelerated. Thus, using the compositions and methods described herein, scuPA can be rendered susceptible to binding by $\alpha_2$MR/LRP without the need to first convert scuPA to tcuPA. No physiological analogue of the activity exhibited by peptide EEIIMD, as described herein, has been reported.

EXAMPLE 2
Models for Testing the Potency of PAI-1 peptide in vivo

Three models have been developed to evaluate the PAI-1 peptide of the invention in vivo.
1) Effect of PAI-1 Peptide on uPA Mediated-fibrinolysis in vivo An in vivo model of clot lysis was developed. In this model, a homogenous preparation of radiolabeled micro-emboli was injected into the tail vein of a mouse. The spontaneous and uPA-mediated clearance of the clots over time was then assessed.

The Materials and Methods used in the experiments presented in this Example are now described.

Preparation of Micro-Emboli

Plasminogen-depleted human fibrinogen was radiolabeled with $^{125}$I using Iodo-beads and the free iodine was removed using a PD-10 column (Pharmacia, Piscataway, N.J.) $^{125}$I-fibrinogen (~40×10$^6$ cpm) was added to 1.2 mL of unlabeled fibrinogen (35 mg/mL final concentration) prior to forming micro-emboli. To form the clot, whole blood from a healthy volunteer was collected in citrate (0.32% final concentration). Plasma was isolated by centrifugation at 1200×g. Plasma (2.5 mL) was mixed with 0.1 mL trace labeled $^{125}$I-human fibrinogen (40 mg; 10 mg/mL final concentration in a glass tube. CaCl$_2$ (20 mM final concentration) and human thrombin (Sigma; 0.2 U/mL, final concentration) were added at room temperature for 1 hour and maintained overnight at 4° C. All subsequent steps were performed at 4° C. as well. The clots were decanted on plastic lids, cut into small pieces and resuspended in 2 mL Kreb's Ringer's buffer (KRB). The clots were homogenized for 30 seconds using a PT-10/35 Polytron homogenizer (Brinkmann Instr., Westbury, N.Y.) at mid-speed. After homogenization, the samples were centrifuged at 2000×g for 15 min. The supernatant was removed and the pellet was resuspended in KRB. A second homogenization was performed at higher speed for 30 seconds and the pellet was washed as described. After the final homogenization, the micro-emboli were suspended in 13 mL KRB-bovine serum albumin (BSA) (3 mg/mL). $^{125}$I-micro-emboli aliquots were stored at 4° C. and were used within 24 hour. The preparation was mixed by repetitive pipetting and allowed to sediment for 5 minutes just prior to use to eliminate any larger particles which remained. The supernatant was split into 200 µl aliquots immediately prior to injection. Random aliquots were selected to characterize the size distribution of the micro-emboli using a ZM Coulter counter (Coulter Electronics, LTD. Hialeah, Fla.).

Mice

Mice having genetic deletions in tissue-type plasminogen activator (tPA$^{-/-}$), urokinase-type plasminogen activator (uPA$^{-/-}$), and the urokinase receptor (uPAR$^{-/-}$), each on a 25% Swiss/75%C57/black background and their respective littermate controls were used (Carneliet et al., 1994, Nature 369:419_424; Dwerchin et al., 1996, J. Clin. Invest. 97:870–878). tPA$^{-/-}$ on a C57/black background wild type C57/black mice and wild type Balb/c mice were obtained from Jackson Laboratories (Bar Harbor, Me.). All of the mice weighed 20–30 g at the time of study. There was no influence of the various genetic backgrounds of the wild type mice with respect to endogenous fibrinolysis.

Plasma Clearance $^{125}$I-micro-emboli (200 µl aliquots containing 15–30,000 cpm) were resuspended by pipetting several times immediately before loading a 21 gauge syringe. Mice were injected via the tail vein and returned to their cages until sacrifice. At various times after injection (10 minutes, 1, 3 and 5 hours), the mice were anesthetized using metofane, and 100 µl of blood was withdrawn by retroorbital puncture into a heparinized capillary pipette. The mice were sacrificed by cervical dislocation. The major organs were harvested immediately, rinsed in saline, dried on Whatman paper and the radioactivity in each tissue was measured. The exact dose (cpm) injected into each mouse was calculated by subtracting the residual radioactivity remaining in the tube and syringe after injection. Radioactivity in the tail of each mouse was counted to verify that the injection was complete. In some experiments, the lungs were obtained at 10 minutes after injection and were fixed in formalin for immunohistochernical staining. In another set of experiments, the lungs were exposed to X-ray film to determine the distribution of radioactivity. In a third series of experiments, the individual lobes from each lung were isolated and the radioactivity therein was assessed.

Recovery Experiments

Two chain urokinase (tcuPA) was obtained from American Diagnostica (Greenwich, Conn.). uPA$^{-/-}$ mice were anesthetized by intraperitoneal injection of Nembutal (50 mg/kg). A polyethylene catheter, siliconized with Sigmacot solution (Sigma Chemical Co. St. Louis, Mo.), was washed with PBS and cannulated in the jugular vein. tcuPA or PBS was infused using a PHD 2000 multi-syringe pump at a rate of 15 µL/min for the first 5 minutes and then 5 µL/minute for 60 minutes. The $^{125}$1-micro-emboli were injected into the tail vein as described above 5 minutes after the infusion was started. The mice were kept under anesthesia throughout the entire experiment. At the completion of the infusion, the mice were sacrificed and the tissues were harvested and counted.

The Results of the experiments presented in this Example are now described.

Figure 7:
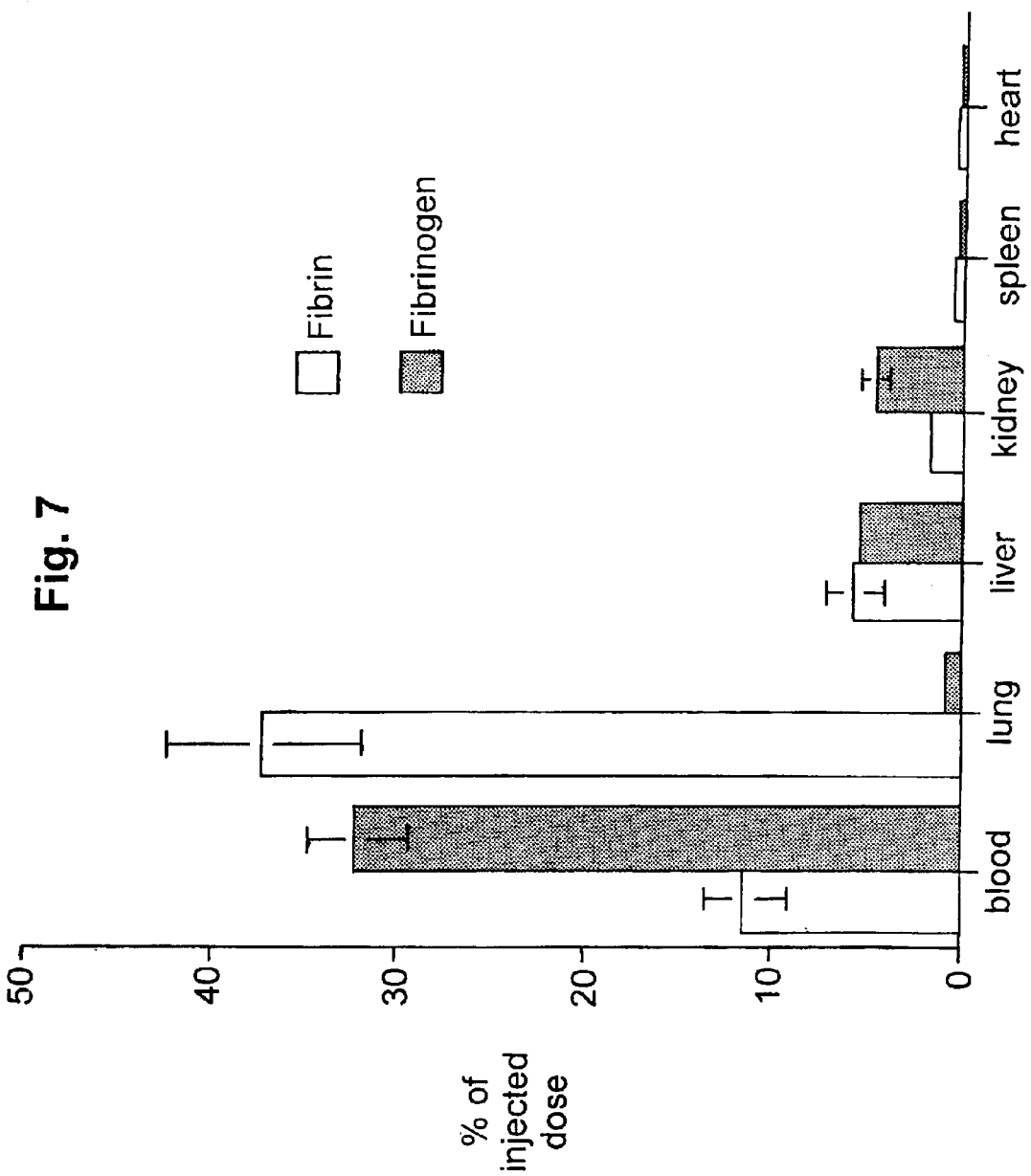
FIG. 7 is a graph depicting a comparison of the distribution of labeled fibrin micro-emboli and radiolabeled fibrinogen.

In FIG. 7 there is shown a comparison of the distribution of labeled fibrin micro-emboli and radiolabeled fibrinogen. The data illustrate that whereas fibrinogen was observed predominantly in the blood, the fibrin clots localized primarily within the lung. This was confirmed by autoradiography of the lungs and by immunohistochemical staining. Both assays demonstrated a homogeneous distribution of radiolabeled fibrin clots in the microvasculature through all lobes.

Figure 8:
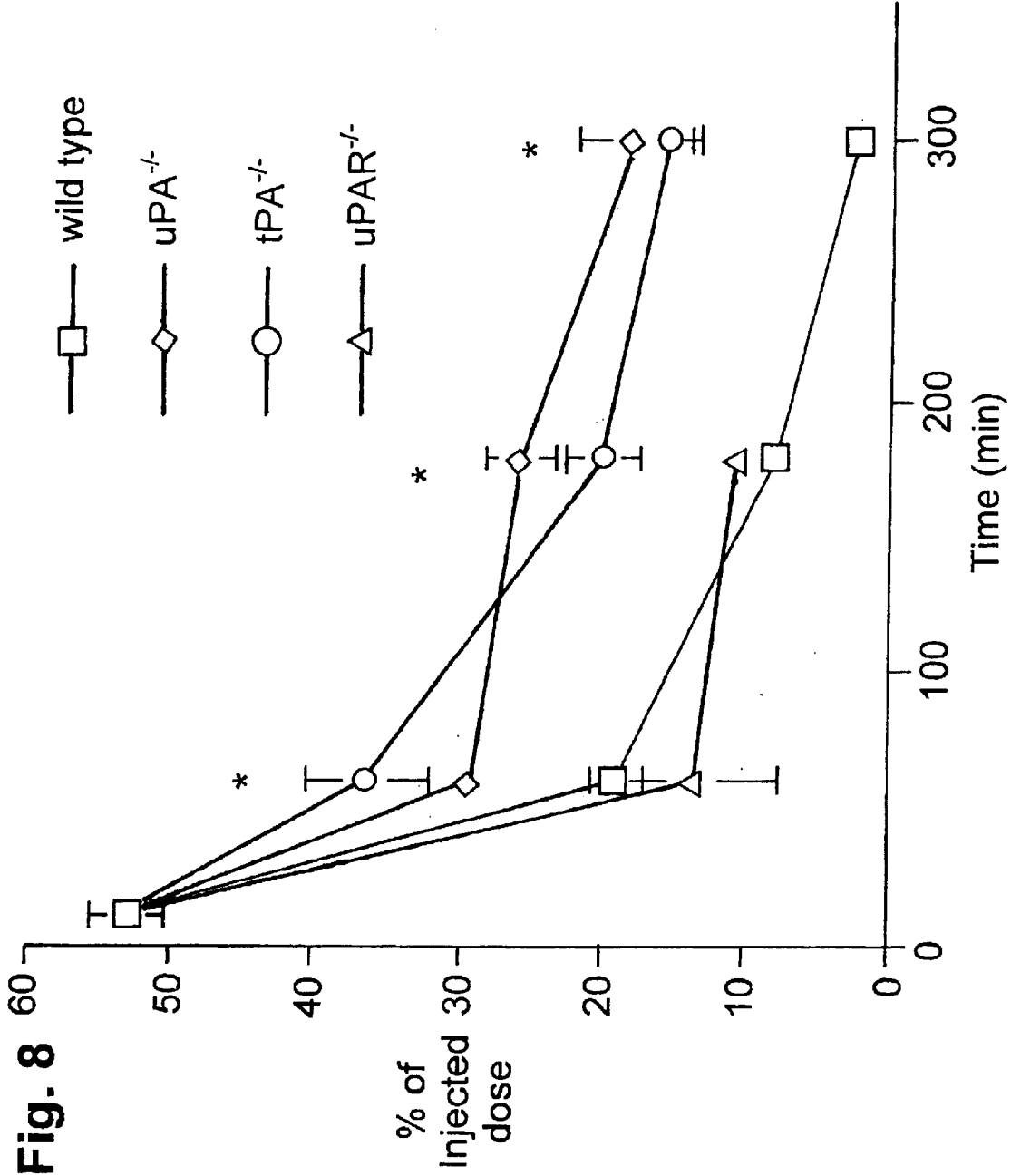
FIG. 8 is a graph depicting clearance of micro-emboli from the lungs of wild type animals and various animals having deletion mutations in tissue-type plasminogen activator (tPA$^{-/-}$), urokinase-type plasminogen activator (uPA$^{-/-}$), and the urokinase receptor (uPAR$^{-/-}$).

In FIG. 8, there is shown the clearance of the micro-emboli from the lungs of wild type animals and animals having various deletion mutations in tissue-type plasminogen activator (tPA$^{-/-}$), urokinase-type plasminogen activator (uPA$^{-/-}$), and the urokinase receptor (uPAR$^{-/-}$). The data clearly demonstrate that fibrinolysis was impaired in mice lacking either urokinase or tPA. This is the first known demonstration of a defect in endogenous pulmonary fibrinolysis in uPA$^{-/-}$ mice.

Figure 9:
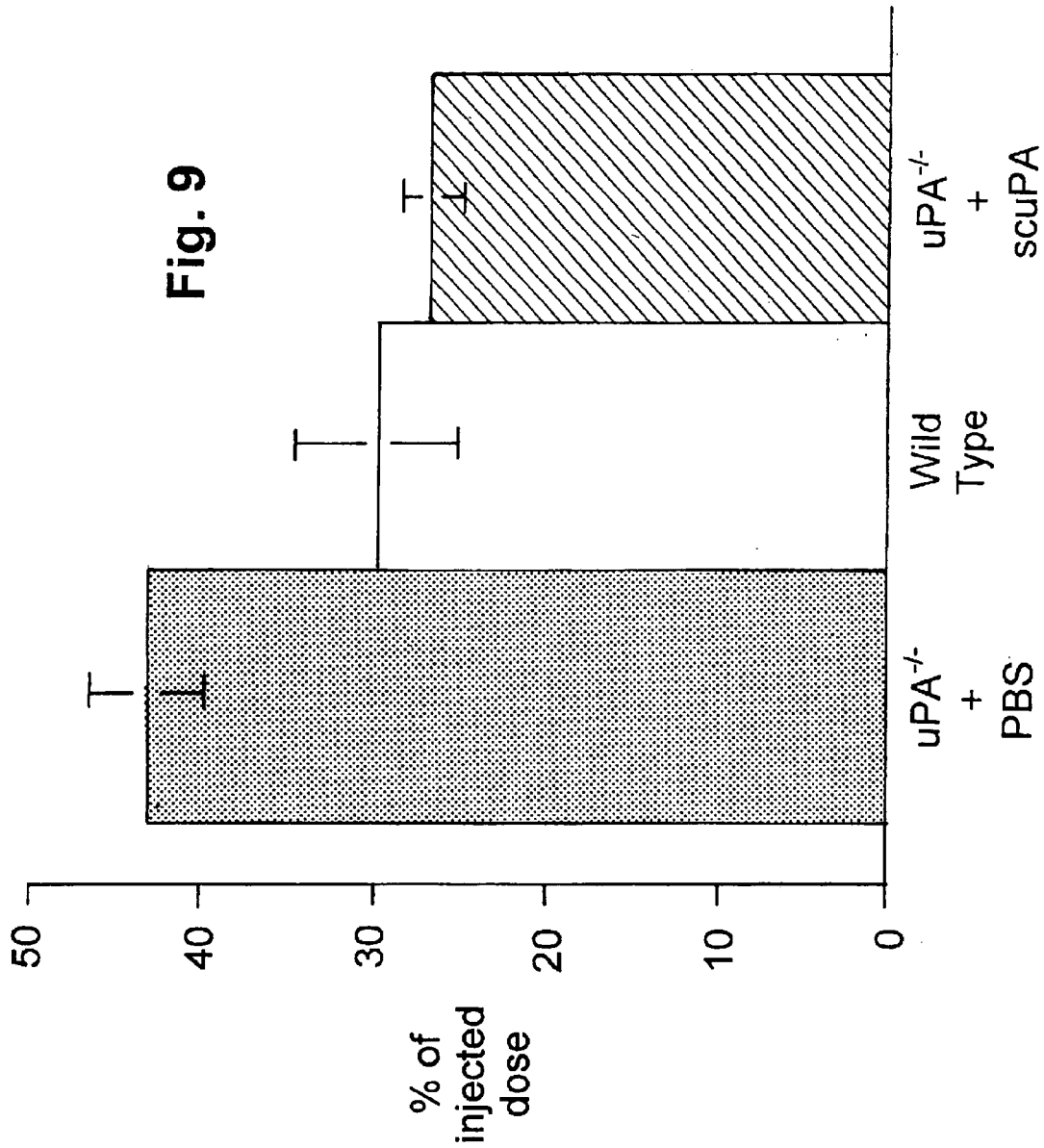
FIG. 9 is a graph depicting data obtained when the phenotype of the urokinase-type plasminogen activator (uPA$^{-/-}$) mice was rescued by infusion of two chain uPA. Clot lysis in the uPA$^{-/-}$ mice was complete.

In FIG. 9, there is shown the results when the phenotype of the uPA$^{-/-}$ mice was rescued by infusion of two chain uPA. Clot lysis in the uPA$^{-/-}$ mice was complete.

This model provides a rapid, i.e., one hour, non-lethal, reproducible, biologically relevant, scuPA-dependent endpoint in a small animal model using human clots.

To determine whether the PAI-I peptide act synergistically with tcuPA to promote fibrinolysis, competition experiments using endogenous PAI-I may be performed. Experiments are conducted in wild type animals by investing the clot and/or the mouse plasma with murine or human PAI-1 and in mice which overexpressing human PAI-I (Eitzman et al., 1996, J. Clin. Invest. 97:232–237). To conduct such experiments, dose-response experiments are performed using PAI-I peptide and a scrambled peptide control in the presence of a constant amount of tcuPA and PAI-1. The peptide is infused immediately before or coincident with tcuPA. The clearance of $^{125}$1-tcuPA may also be measured in the presence of PAI-I peptide. It is hypothesized that this clearance will be impeded since the major pathway for the removal of $^{125}$1-tcuPA is mediated by determinants on PAI-I. It is also hypothesized that the PAI-I peptide should dramatically lessen the amount of urokinase required for clot lysis. In addition, it has recently been reported that clot-bound vitronectin binds and stabilizes the PAI-1 in an active conformation. Therefore, experiments which are designed to determine whether the PAI-I peptide competes for vitronectin binding thereby promoting fibrinolysis by removing active inhibitor from the clot may be performed.

2) The Effect of the PAI-I Peptide on Tumor Cell Adhesion and Metastasis Formation PAI-1 plays an important role in regulating in tumor cell adhesion and thereby regulating tumor metastasis. There is evidence to suggest that this effect is mediated by competition between PAI-I and vironectin for the urokinase receptor, an important mediator of certain β-integrins (Stefansson et al., 1996, Nature 383:441–443; Deng et al., 1996, J. Cell Biol. 134:1563–1571). Recent data indicates that mice with a targeted deletion in PAI-1 exhibit fewer metastases as a result of impaired tumor adhesion (Bajou et al., 1998, Nature Med. 4:923–928). It is hypothesized that the PAI-1 peptide will compete with native PAI-I thereby having an anti-metastatic effect on cells. Further, as the data presented herein establish, the PAI-I peptide accelerates the internalization of uPA by a$_2$MR/LRP which represents a second locus of anti-metastatic activity.

Experiments may be directed to examining the effect of PAI-I peptide on cell adhesion in vitro. The adhesion of U937 cells may be measured by a minor modification of the method described by Li et al. (1995, J. Biol. Chem. 270:30282–30285). Briefly, U937 cells stimulated with TNFα: and labeled with $^3$H-thymidine are added to vitronectin-pretreated or untreated plastic wells in the presence of scuPA (1 nM). To study the anti-adhesive effects, the PAI-1 derived peptide (0–100 µM) or a scrambled peptide control is added contemporaneously with uPA. At various times, the wells are washed, the cells are lysed and the released radioactivity is determined. The potency of the anti-adhesive effect is based on a comparison of the IC50 versus 1 nM scuPA.

As a second step, the effect of the PAI-1 peptide on the migration of endothelial cells through collagen coated membranes as a model of pathologic angiogenesis may be examined. Receptor-associated scuPA may be responsible for urokinase activity on endothelial cells and on other cell types (Barnathan et al., 1990, J. Biol. Chem. 265:2865–2872; Manchanda et al., 1991, J. Biol. Chem. 266:14580–14584). The data presented herein have established that PAI-I peptide promotes scuPA clearance and competes with the pro-adhesive effects of PAI-1. Therefore, this model is effective to test both the anti-adhesive and anti-proteolytic effects of the PAI-1 peptide.

In a third step, the anti-metastatic capacity of the PAI-1 peptide in vivo may be demonstrated. To accomplish this, stable tumor cell lines that express uPA which is PAI-1 resistant have been generated. Specifically, a syngeneic cell line has been developed that coexpresses human uPAR and a plasmin-insensitive scuPA (scuPA-glu$^{158}$). This mutation prevents conversion of uPA to two chain urokinase and thereby assures that any biological activity of this molecule is due to receptor bound and activated single chain uPA. Data have been obtained which establish that scuPA-glu$^{158}$ bound to uPAR is enzymatically active and insensitive to PAI-I in vitro. The tumor cells are injected into syngeneic rats in the presence/absence of PAI-1 peptide or a scrambled peptide control. The growth of the primary tumor and formation of pulmonary metastases is monitored over the subsequent fourteen days. It is predicted that these tumor cells will metastasize readily in the absence of PAI-I peptide but that the peptide will inhibit both their local growth and metastatic capacity through an effect on uPA-mediated cell adhesion and proteolysis.

The disclosures of each and every patent, patent application, and publication cited herein are hereby incorporated herein by reference in their entirety.

While this invention has been disclosed with reference to specific embodiments, it is apparent that other embodiments and variations of this invention may be advised by others skilled in the art without departing from the true spirit and scope of the invention.

What is claimed is:

1. A composition comprising a peptide consisting of the amino acid sequence $X_1X_2X_3X_4X_5X_6X_7X_8$, wherein:

$X_1$ is hydrogen or an amino-terminal blocking group;

$X_2$ is an amino acid selected from the group consisting of D, E, and R;

$X_3$ is an amino acid selected from the group consisting of D and E;
  $X_4$ is I;
  $X_5$ is I;
  $X_6$ is M;
  $X_7$ is an amino acid selected from the group consisting of D and E; and
  $X_8$ is hydrogen or a carboxyl-terminal blocking group.

2. A composition comprising a peptide consisting of the amino acid sequence $X_1X_2X_3X_4X_5X_6X_7X_8$, wherein:
  $X_1$ is hydrogen;
  $X_2$ is E;
  $X_3$ is E;
  $X_4$ is I;
  $X_5$ is I;
  $X_6$ is M;
  $X_7$ is D; and
  $X_8$ is hydrogen.

3. The composition of claim 1, further comprising a pharmaceutically acceptable carrier.

4. A kit comprising a peptide having the amino acid sequence $X_1X_2X_3X_4X_5X_6X_7X_8$, wherein:
  $X_1$ is hydrogen or an amino-terminal blocking group;
  $X_2$ is an amino acid selected from the group consisting of D, E, and R;
  $X_3$ is an amino acid selected from the group consisting of D and E;
  $X_4$ is I;
  $X_5$ is I;
  $X_6$ is M;
  $X_7$ is an amino acid selected from the group consisting of D, E, H, K, and R; and
  $X_8$ is hydrogen or a carboxyl-terminal blocking group; and an instructional material for using the kit.

5. The composition of claim 2, further comprising a pharmaceutically acceptable carrier.

* * * * *